US005419342A

United States Patent [19]

Scott

[11] Patent Number: 5,419,342

[45] Date of Patent: May 30, 1995

[54] ADJUSTABLE RADIATION SHIELD ASSEMBLY FOR PROTECTING THE BREAST OF A PATIENT

[76] Inventor: Christina M. Scott, 3420 Maple Timber Dr., Antioch, Tenn. 37013

[21] Appl. No.: 195,333

[22] Filed: Feb. 14, 1994

[51] Int. Cl.[6] .......... A61F 5/37; G21F 3/02

[52] U.S. Cl. .......... 128/846; 250/516.1; 2/102; 128/849

[58] Field of Search .......... 128/846, 849, 874; 976/DIG. 336, DIG. 337, DIG. 338; 250/516.1, 519.1; 2/2

[56] References Cited

U.S. PATENT DOCUMENTS

| | | | |
|---|---|---|---|
| 2,404,225 | 7/1946 | Green | 250/516.1 |
| 2,494,664 | 1/1950 | Lubow | 250/516.1 |
| 3,052,799 | 9/1962 | Hollands | 250/516.1 |
| 3,093,829 | 6/1963 | De Witt . | |
| 3,154,789 | 11/1964 | Lewis, Jr. | 128/846 |
| 3,233,248 | 2/1966 | Bushnell . | |
| 3,569,713 | 3/1971 | Via, Jr. | 250/516.1 |
| 3,996,620 | 12/1976 | Maine . | |
| 4,196,355 | 4/1980 | Maine . | |
| 4,220,867 | 9/1980 | Bloch, Jr. . | |
| 4,286,170 | 8/1981 | Moti | 250/519 |
| 4,417,146 | 11/1983 | Herbert . | |
| 4,441,025 | 4/1984 | McCoy, Jr. . | |
| 4,843,641 | 7/1989 | Cusick et al. | 2/2 |
| 4,924,103 | 5/1990 | Stein et al. . | |
| 4,938,233 | 9/1990 | Orrison, Jr. | 128/849 |
| 5,028,796 | 7/1991 | Swartz . | |
| 5,274,851 | 1/1994 | Simpkins, Sr. et al. | 2/102 |

OTHER PUBLICATIONS

Catalogue distributed by Alimed, Inc. of Dedham, Mass., p. H77 for a Breast Protector.

*Primary Examiner*—Robert A. Hafer
*Assistant Examiner*—Michael O'Neill
*Attorney, Agent, or Firm*—Marshall & Melhorn

[57] ABSTRACT

An adjustable shield assembly for protecting the breast of a patient from radiation during the radiographic examination of the spinal column is provided. The breast shield assembly includes a right side shield assembly and a left side shield assembly. The shield assemblies each include a generally L-shaped portion, and may be assembled in an adjustable manner to provide an effective radiation shield for the breasts and axillary region of the patient without impeding a radiographic examination of the spinal column.

5 Claims, 3 Drawing Sheets

ADJUSTABLE RADIATION SHIELD ASSEMBLY FOR PROTECTING THE BREAST OF A PATIENT

BACKGROUND OF THE INVENTION

1. Field of the Invention

The invention relates generally to radiation shielding garments and, more particularly, to an adjustable shield assembly for protecting the breast of a patient from radiation, especially during the radiographic examination of the spinal column.

2. Summary of Related Art

In recent years, there has been a growing emphasis on physical screening programs in schools for the early detection of scoliosis. Adolescents whose scoliosis has been identified through such non-radiographic physical examinations often require follow-up surveillance with periodic x-ray evaluation throughout their final growth years. In addition, females have been found to comprise roughly two-thirds of the positive scoliosis population which requires such follow-up treatment. This has led to a progressive increase in the number of x-ray examinations of the spinal column of adolescent females.

It is known that the breast is at greater risk for the development of radiation-induced breast cancer during adolescence than at any other time of life. Unfortunately, that is precisely the period when x-rays are necessary to guide the treatment of scoliosis and provide follow-up information. Increasingly, there are concerns regarding the potential for the development of breast cancer associated with radiation exposure during such periodic x-ray examinations. It is therefore very important to minimize the radiation exposure to the breast, as well as to other radiosensitive organs such as the lymph nodes in the axillary region, during the radiographic examination of the spinal column of scoliosis patients.

Breast shielding is one relatively simple method of directly minimizing the exposure of the breast tissue to radiation during such radiographic examinations. The breast shielding devices used previously have generally been comprised of a strip of a flexible radiation shielding material which is draped around the back of the neck of the patient. One end of the shield lies over one breast and the other end lies over the other breast of the patient. Such breast shields, while providing generally effective anterior shielding of the breasts, lack lateral and posterior shielding, and are therefore ineffective in protecting against any back-scattered radiation. Further, since female adolescent scoliosis patients may be of widely different sizes, multiple breast shields of varying sizes are required in order to obtain a proper fit for every patient.

SUMMARY OF THE INVENTION

The invention relates to a radiation shield assembly for protecting a breast of a patient during a radiographic examination. The shield assembly in accordance with the invention comprises a first, right side shield member formed of a flexible radiation shielding material, and being generally L-shaped with a first leg and a second leg. A second, left side shield member, formed of a flexible radiation shielding material, and being generally L-shaped with a first leg and a second leg, is also provided. An attachment means releasably and adjustably secures the first leg of each shield member to the second leg thereof. The shield assembly is thus adapted so that the respective first legs are draped over the shoulder of the patient, with the second legs both extending across the associated axillary regions of the patient, where the second legs are releasably secured to the respective first legs.

In a preferred embodiment, the right side assembly is comprised of a right anterior shield member and a right posterior shield member, each formed of a flexible radiation shielding material and being generally L-shaped with a first leg and a second leg. A first attachment means is provided for releasably securing the first leg of the right anterior shield member to the first leg of the right posterior shield member. Similarly, a left side assembly is comprised of a left anterior shield member and a left posterior shield member, each formed of a flexible radiation shielding material, and being generally L-shaped with a first leg and a second leg. A second attachment means is provided for releasably securing the first leg of the left anterior shield member to the first leg of the left posterior shield member. Preferably, a third attachment means is provided for releasably securing the right side assembly to the left side assembly.

The radiation breast shield assembly of the invention thus provides an effective means of protecting the breasts and axillary lymph nodes of a patient without impeding a radiographic examination of the spinal column of the patient. Furthermore, the invention provides such a breast shield assembly which is readily adjustable to fit patients of varying size.

BRIEF DESCRIPTION OF THE DRAWINGS

The above, as well as other advantages of the present invention, will become readily apparent to those skilled in the art from the following detailed description of a preferred embodiment when considered in the light of the accompanying drawings, in which.

DESCRIPTION OF THE PREFERRED EMBODIMENT

Figure 1:
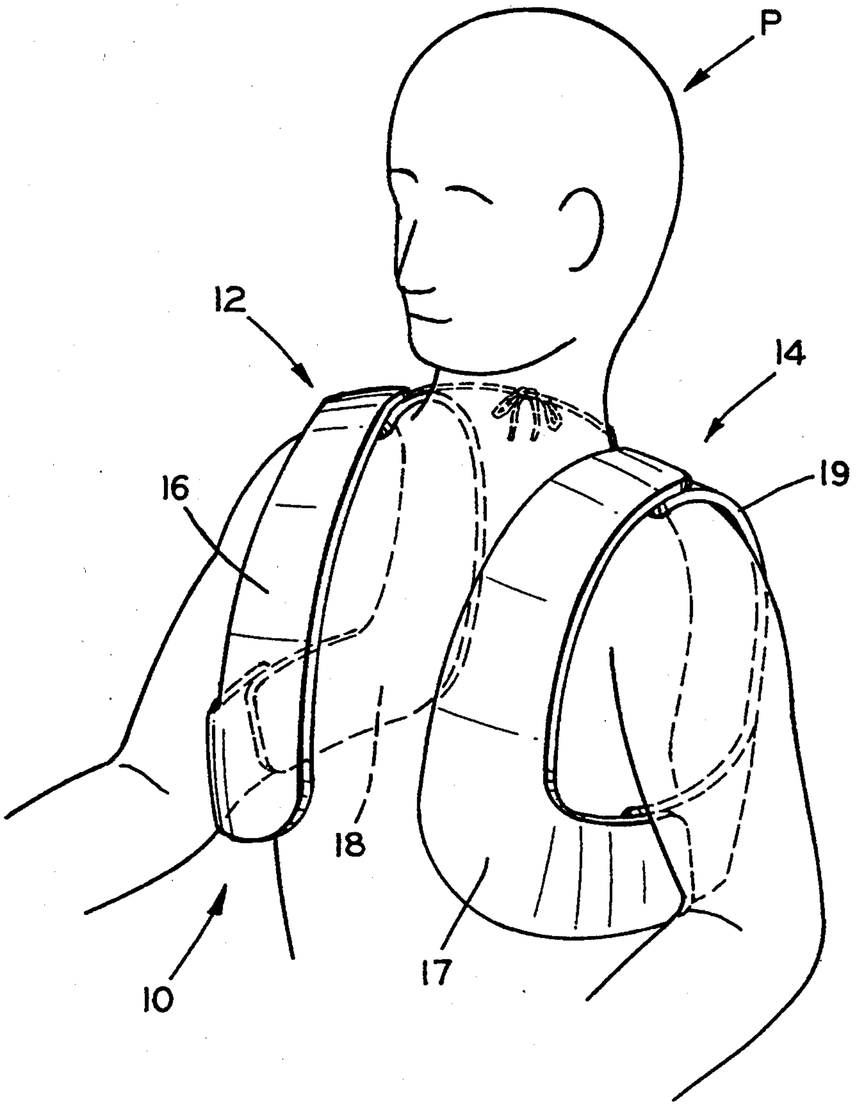
FIG. 1 is a perspective view of the breast shield assembly of the invention as applied to a patient.

Referring now to the drawings, FIG. 1 illustrates the head and torso of a patient P wearing the breast shield assembly of the invention, denoted generally at 10. The breast shield assembly of the invention is more particularly comprised of a right side shield assembly 12 and a left side shield assembly 14, which preferably includes four generally L-shaped radiation shield members: a right anterior shield member 16; a left anterior shield member 17; a right posterior shield member 18; and a left posterior shield member 19. The shielding shield members 16, 17, 18 and 19, more clearly illustrated in FIGS. 2–5 respectively, are assembled as described below to provide an effective radiation shield for the breasts and axillary region of the patient P during a radiographic examination of the spinal column of the patient P.

As illustrated in FIGS. 2–5, in a preferred embodiment each of the shield members 16, 17, 18 and 19 is generally L-shaped. The right anterior shielding shield member 16 is formed with a first leg 20 and a second leg 22. Similarly, the left anterior shield member 17 is formed with a first leg 24 and a second leg 26; the right posterior shield member 18 is formed with a first leg 28 and a second leg 30; and the left posterior shield member 19 is formed with a first leg 32 and a second leg 34.

Figure 6:
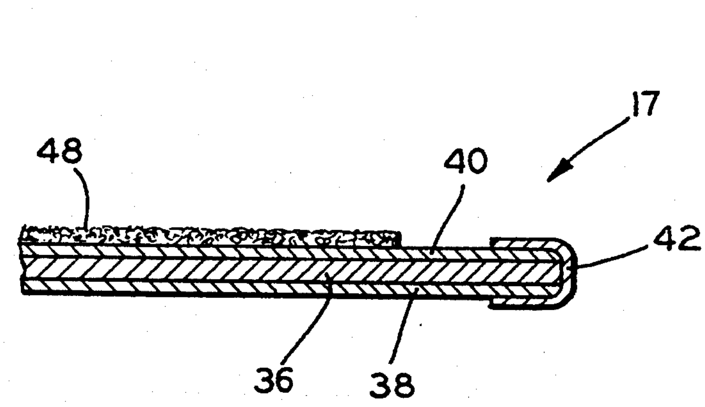
FIG. 6 is a sectional view taken along the line 6—6 of the shield member illustrated in FIG. 3.
Figure 2:
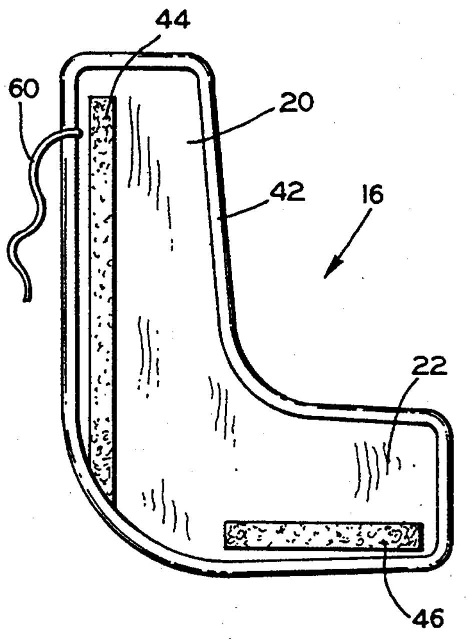
FIG. 2 is an elevational view of the right anterior shield member of the invention.
Figure 3:
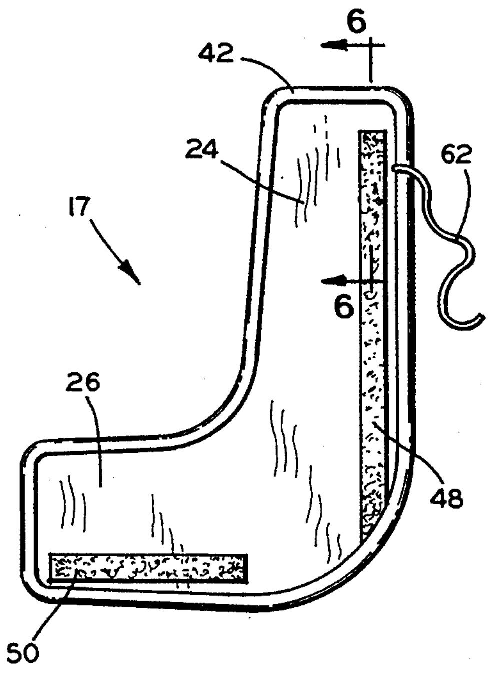
FIG. 3 is an elevational view of the left anterior shield member of the invention.
Figure 4:
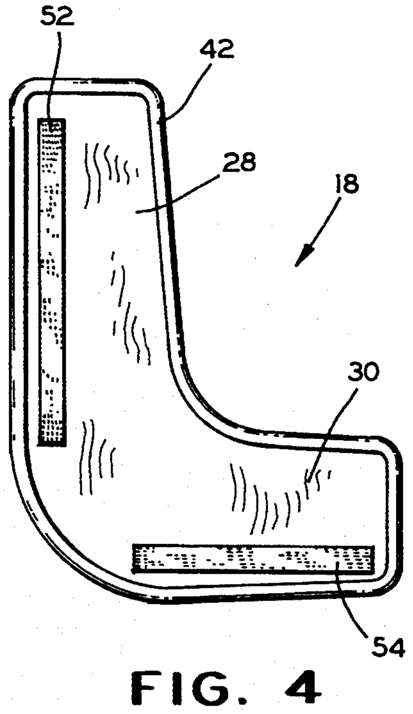
FIG. 4 is an elevational view of the right posterior shield member of the invention.
Figure 5:
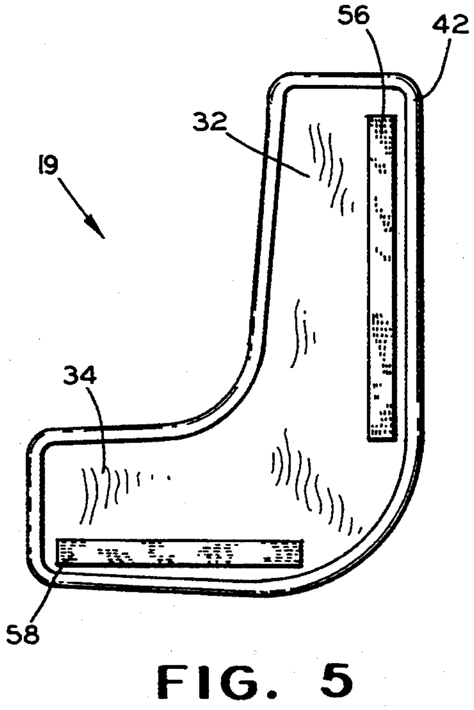
FIG. 5 is an elevational view of the left posterior shield member of the invention.

Preferably, each of the shielding shield members 16, 17, 18 and 19 is comprised of a layer of a flexible radiation shielding material 36, such as rubberized lead or the like. The layer of radiation shielding material 36 is preferably at least 0.5 mm lead equivalent. The layer of radiation shielding material 36 is sandwiched between first and second fabric layers 38 and 40, respectively, as best seen in FIG. 6 with regard to the shield member 17. The fabric layers 38 and 40 may be formed of any suitable fabric, such as cotton, polyester or the like. A binding 42, formed of cotton or other suitable material, is provided about the entire periphery of each of the shield members 16, 17, 18 and 19 by any suitable means, such as with an adhesive or by stitching.

Each of the shield members 16, 17, 18 and 19 is also preferably provided with a releasable and adjustable attachment member secured to each of the legs thereof. Thus, the right anterior shielding shield member 16 is provided with a first attachment member 44 on the first leg 20, and a second attachment member 46 on the second leg 22. Similarly, the left anterior shield member 17 is provided with a first attachment member 48 on the first leg 24, and a second attachment member 50 on the second leg 26; the right posterior shield member 18 is provided with a first attachment member 52 on the first leg 28 and a second attachment member 54 on the second leg 30; and the left posterior shield member 19 is provided with a first attachment member 56 on the first leg 32 and a second attachment member 58 on the second leg 34. The various releasable and adjustable attachment members are preferably formed with a series of attachment means extending along a portion of the associated shield member leg to allow the adjustment of the various attachments described below. In a most preferred embodiment, each of the attachment means is formed of a strip of a "hook" and "loop" type adhering closure material, such as that sold under the VELCRO trademark.

The right anterior shield member 16 and the right posterior shield 18 may thus be releasably and adjustably attached together to form the right shield assembly 12. The first leg 20 of the right anterior shield member 16 is draped over the right shoulder of the patient P and covers the right breast of the patient P, and the first leg 28 of the right posterior shield member 18 is draped over the right shoulder of the patient P. The first leg 20 of the shield member 16 overlaps the first leg 28 of the shield member 18 and is secured thereto by the attachment strip 44, which mates with the complementary attachment strip 52. To enhance patient comfort, where the attachment strips are VELCRO type fasteners, it is preferable to provide the "hook" members on whichever attachment strip faces outwardly from the patient P (for example, as illustrated in FIG. 1, it is preferable to provide the attachment strip 52 on the right posterior shield member 18 with the "hook" members).

Preferably, each of the second legs 22 and 30 extends under the arm of the patient, where the second leg 30 of the shield member 18 is secured to the second leg 22 of shield member 16 by means of the complementary attachment strips 46 and 54 formed on the shield members 16 and 18, respectively.

The left side shield assembly 14 is formed from the left anterior shield member 17 and the left posterior shield member 19 in much the same manner as the right side shield assembly 12. Thus, the first leg 24 of the left anterior shield member 17 is draped over the left shoulder of the patient P and covers the left breast of the patient P, and the first leg 32 of the left posterior shield member 19 is draped over the left shoulder of the patient P. The first leg 24 of the shield member 17 overlaps the first leg 32 of the shield member 19 and is secured thereto by the attachment strip 48, which mates with the complementary attachment strip 56.

Preferably, each of the second legs 26 and 34 extends under the arm of the patient, where the second leg 26 of the left anterior shield member 17 is secured to the second leg 34 of the left posterior shield member 19 by means of the complementary attachment strips 50 and 58 formed on the shield members 17 and 19, respectively.

It will appreciated that the right side shield assembly 12 and the left side shield assembly 14 are both readily adjustable both as to the length along the torso of the patient and about the circumference thereof, so that both of the shield assemblies may be adjusted to properly fit patients having a wide variety of torso lengths and circumferences.

For an anterior or posterior radiograph, all four of the shield members 16, 17, 18 and 19 are employed as described above. The right side shield assembly 12 and the left side shield assembly 14 are provided with complementary means for releasably attaching the two side assemblies 12 and 14. Preferably, the first leg 42 of the right anterior shield member 16 is provided with an attachment means 60, such as the tie illustrated in FIG. 2, which may be secured to the complementary attachment means 62 provided on the first leg 24 of the left anterior shield member 17. The two side assemblies 12 and 14 may be releasably secured together by joining the ties 60 and 62 across the upper back of the patient P.

When assembled on the patient P, each of the first legs 20, 24, 28 and 32 shields the breast area of the patient P from both direct and back-scattered radiation. The mated pairs of second legs (22 with 30, and 30 with 34) shield the respective axillary areas, including the lymph nodes, of the patient P.

For a lateral radiograph, the associated, or even both of, the posterior shield members 18 and 19 is removed from the patient. The right and left anterior shield members 16 and 17 remain joined together by means of the complementary attachment means 60 and 62. Further, the second leg of the associated anterior shield member (the second leg 22 for a right lateral radiograph, and the second leg 26 for a left lateral radiograph) may be folded back over the associated first leg to expose a lateral view of the spinal column of the patient.

Figure 7:
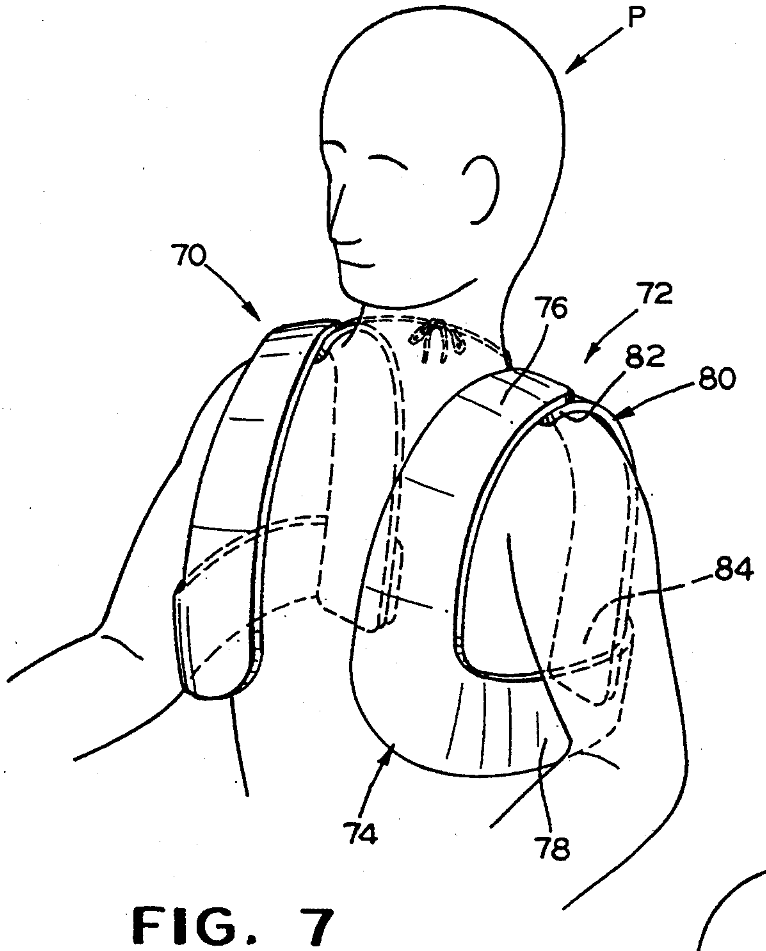
FIG. 7 is a perspective view of an alternate embodiment of the breast shield assembly of the invention as applied to a patient.

In an alternate embodiment of the invention illustrated in FIG. 7, only one member of each of the right side shield assembly 70 and the left side shield assembly 72 is generally L-shaped. Thus, the left anterior shield member 74 includes a first leg 76 and a second leg 78, while the left posterior shield member 80 is formed of a generally straight section having a first end 82 and a second end 84. The first leg 76 of the member 74 is secured to the first end 82 of the member 80 in the same manner as described above. The second leg 78 of the member 74 is formed of sufficient length to extend under the arm and to the posterior of the patient P to overlap the member 80 proximate the second end 84 thereof. It will be appreciated that, alternatively, the left posterior shield member 80 could be formed with a second leg of sufficient length to extend to overlap the anterior member 74, so that a second leg on the anterior member 74 was unnecessary. Attachment members as described above are provided on the various shield members. The right side shield assembly 70 is similarly constructed, and is therefore not discussed in further detail.

Figure 8:
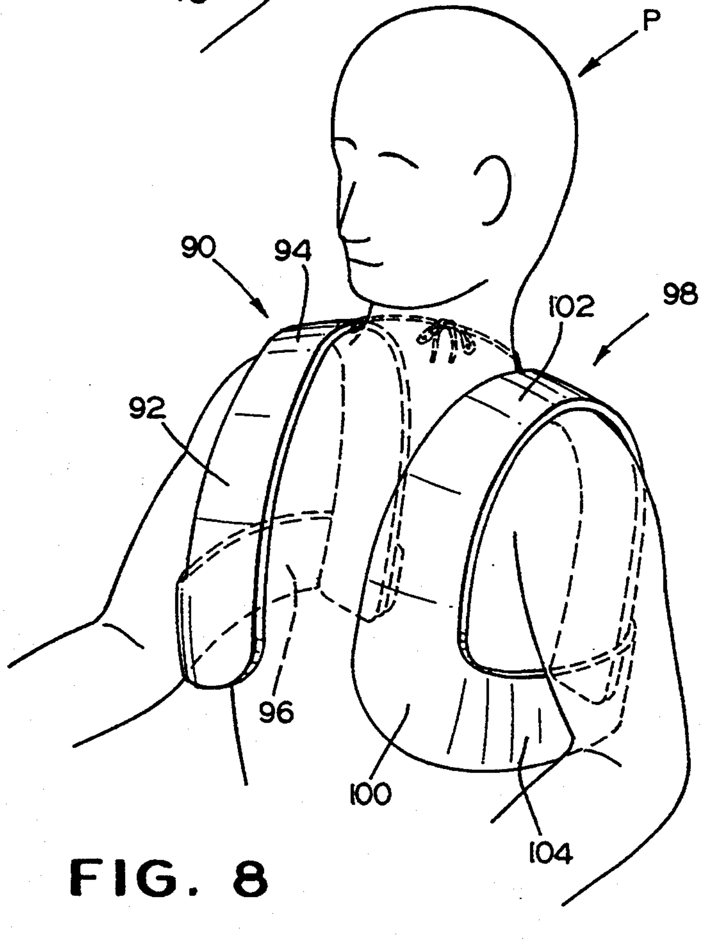
FIG. 8 is a perspective view of a further embodiment of the breast shield assembly of the invention as applied to a patient.

Moreover, in a further embodiment illustrated in FIG. 8, the right side shield assembly 90 is formed of a single, generally L-shaped shield member 92 having a first leg 94 and a second leg 96, the left side shield assembly 98 is formed of a single, generally L-shaped shield member 100 having a first leg 102 and a second leg 104. The first legs 94 and 102 of the right and left shield members 92 and 100 are draped over the respective right and left shoulders of the patient P. The first legs 94 and 102 are formed of sufficient length to extend from the respective breast, over the respective shoulder, and part way down the back of the patient P. The second legs 96 and 104 of the right and left shield members 92 and 100, respectively, extend under the arm and towards the posterior of the patient P to overlap the first legs 94 and 102, respectively. The ends of the first legs 94 and 102 are thus releasably and adjustably secured to the respective second legs 96 and 104 by means of attachment members as described above.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A radiation shield for protecting the breast of a person during a radiographic examination, comprising:

a first shield member formed of a flexible radiation shielding material, and including a generally L-shaped portion having a first leg and a second leg; and a second shield member formed of a flexible radiation shielding material, and including a generally L-shaped portion having a first leg which overlaps the first leg of said first shield member and a second leg which overlaps the second leg of said first shield member;

said overlapping first legs being detachably and adjustably connected to one another by at least one pair of complementary adhering closure members providing an adjustable combined length of said first legs, and said overlapping second legs being detachably and adjustably connected to one another by at least one pair of complementary adhering closure members providing an adjustable combined length of said second legs.

2. A radiation shield for protecting the breasts of a person during a radiographic examination, comprising:

a right side assembly including first and second shield members and a first attachment means, said first shield member being formed of a flexible radiation shielding material, and including a generally L-shaped portion having a first leg and a second leg, and said second shield member being formed of a flexible radiation shielding material, and having a first end and a second end, said first attachment means detachably and adjustably securing the first leg of said first shield member to said second shield member;

a left side assembly including third and fourth shield members and a second attachment means, said third shield member being formed of a flexible radiation shielding material, and including a generally L-shaped portion having a first leg and a second leg, and said fourth shield member being formed of a flexible radiation shielding material, and having a first end and a second end, said second attachment means detachably and adjustably securing the first leg of said third shield member to said fourth shield member; and third attachment means for detachably and adjustably securing said right side shield assembly to said left side shield assembly, further comprising a fourth attachment means for detachably and adjustably securing the second leg of said first shield member to said second shield member, and a fifth attachment means for detachably and adjustably securing the second leg of said third shield member to said fourth shield member.

3. A radiation shield as defined in claim 2, wherein said third attachment means is comprised of an attachment member secured to the first leg of said first and shield member and a complementary attachment member secured to the first leg of said third shield member.

4. A radiation shield as defined in claim 2, wherein said second shield member is formed with a generally L-shaped portion having a first leg and a second leg, and said fourth shield member is formed with a generally L-shaped portion having a first leg and a second leg.

5. A radiation shield as defined in claim 4, wherein said first attachment means detachably and adjustable secures the first leg of said first shield member to the first leg of said second shield member.

* * * * *